US 8,576,399 B2

(12) United States Patent
Andelic et al.

(10) Patent No.: US 8,576,399 B2
(45) Date of Patent: Nov. 5, 2013

(54) METHOD AND APPARATUS FOR TURBIDITY MEASUREMENT

(75) Inventors: Edin Andelic, Stuttgart (DE); Rudiger Frank, Haigerloch (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 475 days.

(21) Appl. No.: 12/736,379

(22) PCT Filed: Apr. 9, 2009

(86) PCT No.: PCT/EP2009/054322
§ 371 (c)(1),
(2), (4) Date: Oct. 1, 2010

(87) PCT Pub. No.: WO2009/125003
PCT Pub. Date: Oct. 15, 2009

(65) Prior Publication Data
US 2011/0043807 A1 Feb. 24, 2011

(30) Foreign Application Priority Data
Apr. 11, 2008 (DE) .................. 10 2008 018 592

(51) Int. Cl.
*G01N 21/00* (2006.01)
(52) U.S. Cl.
USPC .......................................... 356/441
(58) Field of Classification Search
USPC .................................. 356/441–442
See application file for complete search history.

(56) References Cited

U.S. PATENT DOCUMENTS

| 5,012,119 A | 4/1991 | Rhiner |
| 5,140,168 A | 8/1992 | King |
| 5,373,367 A | 12/1994 | DeGunther |
| 5,416,581 A | 5/1995 | Kanngiesser |
| 6,803,594 B2 * | 10/2004 | Spolaczyk et al. ............ 250/574 |
| 2006/0061765 A1 | 3/2006 | Rezvani |
| 2007/0239367 A1 * | 10/2007 | Odegard et al. ................. 702/30 |

FOREIGN PATENT DOCUMENTS

| DE | 2 363 432 | 6/1984 |
| DE | 42 32 957 C2 | 11/1993 |
| DE | 41 42 938 C2 | 4/1995 |
| DE | 197 18 875 C1 | 10/1998 |
| EP | 0 707 247 A1 | 4/1996 |
| GB | 2 355 524 A | 4/2001 |
| WO | WO 01/63253 A1 | 8/2001 |
| WO | WO 2008/006578 A1 | 1/2008 |

* cited by examiner

*Primary Examiner* — Tara S Pajoohi Gomez
(74) *Attorney, Agent, or Firm* — Bacon & Thomas, PLLC

(57) ABSTRACT

A method for turbidity measurement in a measured medium uses a turbidity sensor, which comprises at least a first and a second emitter and at least a first and a second detector. The first and the second emitters are excited one after the other to produce light signals directed into the measured medium; wherein each light signal travels along a first propagation path through the measured medium to the first detector, and is converted by such into a first detector signal; and travels along a second propagation path through the measured medium to the second detector, and is converted by such into a second detector signal. A turbidity value is ascertained based on the first and the second detector signals; wherein, by means of at least one additional detector, to which at least one of the light signals travels along an additional propagation path, an additional detector signal is ascertained, and, on the basis of the additional detector signal, the turbidity value is checked as regards its plausibility.

20 Claims, 6 Drawing Sheets

METHOD AND APPARATUS FOR TURBIDITY MEASUREMENT

TECHNICAL FIELD

The invention relates to a method and to an apparatus for turbidity measurement. The method and apparatus can be applied in a gaseous or liquid, measured medium.

BACKGROUND DISCUSSION

Turbidity arises in gases or liquids through the presence of dispersed materials. Turbidity can be ascertained by interaction between electromagnetic radiation and the measured medium, for example, either by measuring the weakening in intensity of a light signal which penetrates the medium (turbidimetry), or by measuring the intensity of light which is scattered on the dispersed particles (nephelometry). In the case of nephelometry, the intensity of the scattered light is ascertained at an angle (for example, 90°) to a measuring light beam radiated from an emitter.

The term, "light", means here and in the following not only electromagnetic radiation of the visible spectral range, but also electromagnetic radiation of any wavelength, especially light in the infrared wavelength range.

In this context, the use of diodes as emitters and detectors is known. In such case, a light-emitting diode for producing a measuring light beam which lies within a suitable wavelength range (e.g. infrared radiation between 800 and 900 nm) is used as an emitter. As a detector, a photodiode can be correspondingly applied, which produces from the received, scattered light a detector signal (for example, a photocurrent or a photovoltage). The signal strength of the detector signal (here the photocurrent level or the level of the photovoltage), depends on the level of the intensity of the light reaching the detector diode, (thus, in the case of nephelometry, the intensity of the scattered light). This, in turn, correlates directly with the particle size and the concentration of the dispersed materials.

From the detector signal, a turbidity value can thus be determined for the measured medium to be examined. Because of the multiple scattering in turbid media, this turbidity value does not depend linearly on the concentration of the dispersed materials, (referred to in the following as "solids concentration"). Consequently, in order to be able to assign a solids concentration to a turbidity value, a calibration must be performed, for example, by means of comparison with a standard solution.

In the case of turbidity measurements in highly turbid measured media—for example, in slurries of a clarification plant—disturbances of the measuring—such as, for example, those caused by fouling of the turbidity sensor or by component fluctuations—can bring about corruption of the measurement results.

In the case of known methods for turbidity measurement, the use of two or more measuring paths serves to compensate for fouling of the measuring optics or for component fluctuations. Such method are described, for example, in DE 42 32.957 C2, DE 41 42 938 C2 and U.S. Pat. No. 5,140,168.

The turbidity measurement method described in these documents functions according to the four beam, alternating light principle. The sensor applied in such case possesses two emitters and detectors, which, in each case, lie opposite one another. When the emitters are operated one after the other, the two detectors in each case first receive two light signals (which are changed through interaction with the measured medium) from the first emitter and, thereafter, two corresponding signals from the second emitter. The detectors convert the received signals into detector signals, for example, into a photovoltage or a photocurrent. From the detector signals or from values derived therefrom, a turbidity value is ascertained.

In such case, a detector can receive a light signal which travels to the detector from an emitter along a direct propagation path, and the signal's intensity is weakened only by light losses from scattering. A detector can, however, also receive from an emitter along an indirect propagation path a light signal which has been scattered on dispersed particles of the measured medium.

A measuring of the turbidity of a measured medium according to the four beam, alternating light method thus includes a sequential excitation of the emitters, a producing of detector signals by the two detectors, and the ascertaining of a turbidity value from the detector signals.

For ascertaining the turbidity value, in the method described in the previously named documents, the signals, in each case, obtained along a direct propagation path upon excitation, in each case, of one of the emitters are multiplied with one another, and the resulting product divided by the product of the detector signals obtained along the indirect propagation path, in order to form a ratio. This ratio is a measure for the turbidity, and thus for the concentration of dispersed particles. In the concrete case of a suspension of solid particles in a liquid or gaseous medium, the concentration of dispersed particles is also called the "solids concentration". Through this evaluation of the detector signals, component fluctuations or disturbances from fouling of the sensor can, up to a certain degree, be eliminated. Consequently, the four beam, alternating light method is, up to a certain degree, insensitive to such disturbances.

On the other hand, the low sensitivity of the turbidity value ascertained by means of the four beam, alternating light method to disturbances has the affect, that a self-diagnosis of the turbidity sensor on the basis this turbidity value leads only to inexact results, since only larger disturbances of the components or strong foulings make themselves noticeable in the turbidity value.

The sensor described in DE 41 42 938 C2 for turbidity measurements according to the four beam, alternating light method can, therefore, be checked between turbidity measurements with regard to the functioning of the light emitters and the light receivers. This reviewing cannot, however, occur during the measurement operation of the sensor, and, thus, also cannot be taken into consideration for an immediate plausibility checking of an ascertained turbidity value.

SUMMARY OF THE INVENTION

An object of the invention is, consequently, to overcome the disadvantages of the method known in the state of the art. A method should especially be given, which enables a self-diagnosis of an apparatus for turbidity measurement functioning according to the four beam, alternating light method, and/or a method by which deductions concerning the plausibility of an ascertained turbidity value are possible.

This object is achieved by a method for turbidity measurement in a measured medium by means of an apparatus for turbidity measurement, wherein this apparatus comprises at least a first and a second emitter, and at least a first and a second detector; wherein the first and second emitters are excited one after the other, in order to produce light signals directed into the measured medium; and wherein each light signal travels along a first propagation path through the measured medium to the first detector, and is converted by the first detector into a first detector signal, and travels along a second propagation path through the measured medium to the second detector, and is converted by this second detector into a second detector signal; wherein a turbidity value is ascertained on the basis of the first and second detector signals; and wherein, by means of at least one additional detector, to which at least one of the light signals travels along an additional propagation path, a supplemental detector signal is ascertained, and, on the basis of the additional signal, the turbidity value is checked as regards its plausibility.

The first, the second and the additional propagation paths are, especially, mutually differing propagation paths.

"Checking the plausibility of a turbidity value" means, especially, the ascertaining of a probability with which a turbidity value in question reflects the actual turbidity of the measured medium.

Especially, in the case of exciting the first emitter, a turbidity value is ascertained from the detector signals of the first and second detectors, and, in the case of exciting the second emitter, a turbidity value is ascertained from the detector signals of the first and second detectors. The light signal of the first and/or the second emitter travels to the additional detector, and is converted by this into a supplemental detector signal, which is taken into consideration for plausibility checking of the turbidity value.

Rather than use the immediate detector signals, values can first be derived from the detector signals, and these derived values used for ascertaining the turbidity value. A value for determining a turbidity value which is derived from an immediate detector signal, can, for example, be a detector signal which is digitized via an analog/digital-transducer, or an intensity value calculated from the immediate detector signal or from a digitized detector signal. If the immediate detector signal is a photocurrent or a photovoltage, these can be converted before digitizing into a corresponding voltage or a corresponding electrical current. Fundamentally, other values which are derived and/or calculated from the detector signals are also thinkable. Consequently, values derived from the immediate detector signals can also basically be used for ascertaining a turbidity value. For plausibility checking, in addition to the detector signal itself, values derived therefrom can also be used. Here and in the following, the term "detector signal", where not expressly otherwise defined, consequently refers, in addition to the immediate detector signal, also to values derived from an immediate detector signal.

In an embodiment of the method, the at least one additional detector receives a light signal changed by the measured medium. This has the advantage that a supplemental detector signal produced from this light signal can be evaluated as additional information, which is independent of the detector signals of the first and second detectors and yet still concerns the turbidity of the measured medium, so that it can be compared with the ascertained turbidity value. In such case, a changed light signal can be a light signal which is weakened in intensity and which travels along a direct propagation path from the emitter, or a light signal which is scattered on dispersed particles along an indirect propagation path.

In an additional embodiment, the at least one additional detector receives the light signal of an emitter along a propagation path outside of the measured medium. In this way, during operation, the emitter can directly be checked or monitored as regards intensity fluctuations of the light signal transmitted by the emitter.

In a further development of the method, the turbidity value is ascertained from the detector signals of the first and second detectors according to the formula $$W_1 = \frac{I_{1\_1} \cdot I_{2\_2}}{I_{1\_2} \cdot I_{2\_1}} \tag{1}$$

wherein $I_{1\_1}$ is the detector signal of the first detector in the case of excitation of the first emitter, wherein $I_{1\_2}$ is the detector signal of the first detector in the case of excitation of the second emitter, wherein $I_{2\_1}$ is the detector signal of the second detector in the case of excitation of the first emitter, and wherein $I_{2\_2}$ is the detector signal of the second detector in the case of excitation of the second emitter.

The registering of detector signals and ascertaining of a turbidity value from the detector signals can occur via an electronic evaluating unit.

In an additional embodiment of the method, used as additional detectors are a third and a fourth detector, to which the light signals of the first emitter and the second emitter travels along a third propagation path through the measured medium and along a fourth propagation path through the measured medium, respectively; wherein the third detector converts the light signal into a third detector signal, and the fourth detector converts the light signal into a fourth detector signal; and wherein, from the third and the fourth detector signals, an additional turbidity value is ascertained.

Especially, the first, second, third and fourth propagation paths differ from one another.

In a further development of this embodiment, the additional turbidity value is ascertained according to the formula $$W_1 = \frac{I_{3\_1} \cdot I_{4\_2}}{I_{3\_2} \cdot I_{4\_1}} \tag{2}$$

wherein $I_{3\_1}$ is the detector signal of the third detector in the case of excitation of the first emitter, wherein $I_{4\_2}$ is the detector signal of the fourth detector in the case of excitation of the second emitter, wherein $I_{3\_2}$ is the detector signal of the third detector in the case of excitation of the second emitter, wherein $I_{4\_1}$ is the detector signal of the fourth detector in the case of excitation of the first emitter.

Thus, in addition to the first turbidity value ascertained according to the four beam, alternating light method, a further turbidity value is ascertained according to the four beam, alternating light method, which can be used for comparative purposes, especially for testing the plausibility of the first turbidity value.

In an advantageous further development, the third and fourth detectors are arranged in such a manner, that they receive at a different angle from the first and the second detectors light scattered in the measured medium. In this way, the two turbidity values react in a different way to disturbances (for example, to disturbances which are caused by a large particle temporarily affecting the sensor).

In a further development of this embodiment, the additional turbidity value is compared with the turbidity value ascertained from the detector signals of the first and second detectors. This comparison is used for self-diagnosis of the turbidity sensor. In the case of a deviation, the presence a disturbance can be assumed.

The turbidity values can be compared, for example, with one another by ascertaining the solids concentrations corresponding to the turbidity values and taking the difference between the first and the second solids concentrations. For testing the plausibility of the turbidity values, the difference is compared with a predetermined threshold value. The solids concentrations are ascertained on the basis of calibration data.

In such case, the threshold value is predetermined in such a way, that an exceeding of the threshold value represents an inacceptable deviation of the solids concentrations from one another, as obtained from the turbidity values.

In an advantageous further development, an error report is output when the difference in the solids concentrations exceeds the predetermined threshold value.

Alternatively or additionally, the turbidity measurement can be repeated when the difference exceeds the predetermined threshold value.

In an additional embodiment of the method, at least one of the detector signals is compared with a desired value. Through evaluation of at least one or more individual detector signals by comparison with a desired value, disturbances which occur in the individual propagation paths of the light signals can specifically be detected.

In a further development, a number of n detector signals is selected from all detector signals used for ascertaining a turbidity value and from the signals of the additional detectors, and the selected detector signals are represented as coordinates of a measured value point in an n-dimensional coordinate system, or as components of a measured value vector in an n-dimensional vector space.

In a further development, a distance of the measured value point or the measured value vector from a predetermined n-dimensional region of the point space or the vector space is ascertained. If the predetermined n-dimensional region is a region which preferably includes plausible measured value points or vectors (i.e. points or vectors which represent measured values which are not degraded by any disturbances, or perhaps degraded by at least one disturbance which is still tolerable as regards the accuracy of measurement), too strong deviations of the measured value point or the measured value vector, or of individual coordinates or components can be detected. Such too strong deviations mean disturbances in the measuring, which are active in individual propagation paths. If the determining of the distance reveals that the measured value point or measured value vector lies within the predetermined n-dimensional region, the measured value can be classified as plausible.

In a further development, the n-dimensional region is ascertained from a model, or learned on the basis of a machine learning method.

In an additional embodiment, the newly ascertained measured value point or measured value vector is used for fitting the predetermined n-dimensional region, especially when the n-dimensional region is learned by means of a machine learning method. From changes (such as distortions or shiftings) of the n-dimensional region which result while recording the new measured value vector, conclusions can be drawn concerning a newly occurring disturbance, as well as concerning the type of this disturbance.

In an additional embodiment, on the basis of the distance of the measured value point or the measured value vector from the predetermined n-dimensional region, a plausibility checking, especially a machine plausibility checking, of the turbidity value ascertained from the detector signals can be performed. This can be done, for example, by the electronic evaluating unit.

The object is furthermore achieved by an apparatus for measuring the turbidity of a measured medium, wherein this apparatus includes: At least a first and a second emitter, and at least a first and a second detector; wherein the emitters and the detectors are arranged with respect to one another in such a manner, that light signals produced by the emitters and directed into the measured medium travel, in a first case, along a first propagation path through the measured medium to the first detector, and, in a second case, along a second propagation path through the measured medium to the second detector; wherein the apparatus includes at least one additional detector, to which there travels along an additional propagation path a light signal, which is produced by at least one emitter. By means of the additional detector, a supplemental detector signal can be registered and used for self-diagnosis of the apparatus.

Especially, the first and second and the additional propagation paths differ from one another.

In an advantageous further development, the apparatus includes an evaluating unit, especially an electronic evaluating unit, which is designed to determine a turbidity value of the measured medium from detector signals of the first and second detector, and wherein the evaluating unit is furthermore designed to check the plausibility of the turbidity value on the basis of the detector signal produced by the additional detector.

In an embodiment, the additional detector is arranged with respect to the emitter in such a manner, that it receives from at least one emitter a light signal changed by the measured medium.

In an alternative embodiment, the additional detector is arranged with respect to the emitter in such a manner, that it receives a light signal of at least one emitter along a propagation path outside of the measured medium.

In an additional embodiment, the first emitter and the first detector are arranged next to one another, and the second emitter and the second detector are arranged as mirror images of the first emitter and the first detector. In this way, the two detectors receive at the same angle a light signal scattered in the measured medium.

In a further development of this embodiment, a third and a fourth detector are additionally arranged in such a manner, that the second emitter, the second detector and the fourth detector are arranged as mirror images of the first emitter, the first detector and the third detector. Such an apparatus permits the ascertaining of two turbidity values according to the four beam, alternating light method. Since the third and fourth detectors receive scattered light in the measured medium at a different angle from the first and second detectors, two different turbidity values are obtained, which are based on different calibration models. The different turbidity values are, thus, independent of one another. Disturbances which only make themselves noticeable in one of the two turbidity values can thus be registered.

The emitters and detectors, which are arranged as mirror images, are advantageously all arranged mirror-symmetrically with respect to the same mirror-symmetrical plane. This can, for example, in the case of an apparatus for turbidity measurement with a circularly shaped cross section, extend along a circle diameter of the cross section.

In an advantageous further development of this embodiment, the first emitter is, in its excited state, consequently designed to direct a light beam (especially a light ray bundle) with a main beam direction into the measured medium, wherein the normal of a face of the first detector is arranged at a first angle to the main beam direction, and wherein the normal of a face of the third detector is arranged at a second angle to the main beam direction, and wherein the first angle differs from the second angle.

As regards the orientation of the faces of the detectors relative to the main beam direction of the ray bundle transmitted from the emitters which are switched on, the first and the third detectors are, advantageously, also arranged mirror-symmetrically with respect to the second and fourth detectors with regard to a mirror plane determined by a circle diameter of the circularly shaped cross section of the apparatus for turbidity measurement, and by a line parallel to the main beam direction of the emitter signal.

In an additional embodiment, the emitters are light-emitting diodes and the detectors are photodiodes.

In an advantageous embodiment, the evaluating unit includes a learning memory, especially a neural network. Such a learning memory can be designed to store the detector signals of the individual detectors, and to learn a signal range, in which plausible measured values occur can. It can furthermore be designed to compare newly registered detector signals with the learned signal range, and, on the basis of this comparison, to detect whether disturbances have occurred during the turbidity measurement. The learning memory can, on the basis of the deviation of each individual detector signal from the learned signal range, especially ascertain the presence of a particular type of disturbance, e.g. a fouling of the sensor or a fluctuation of an individual component.

BRIEF DESCRIPTION OF THE DRAWINGS

The invention will now be explained in greater detail on the basis of the appended drawing, the figures of which show as follows.

DETAILED DISCUSSION IN CONJUNCTION WITH THE DRAWINGS

Figure 1:
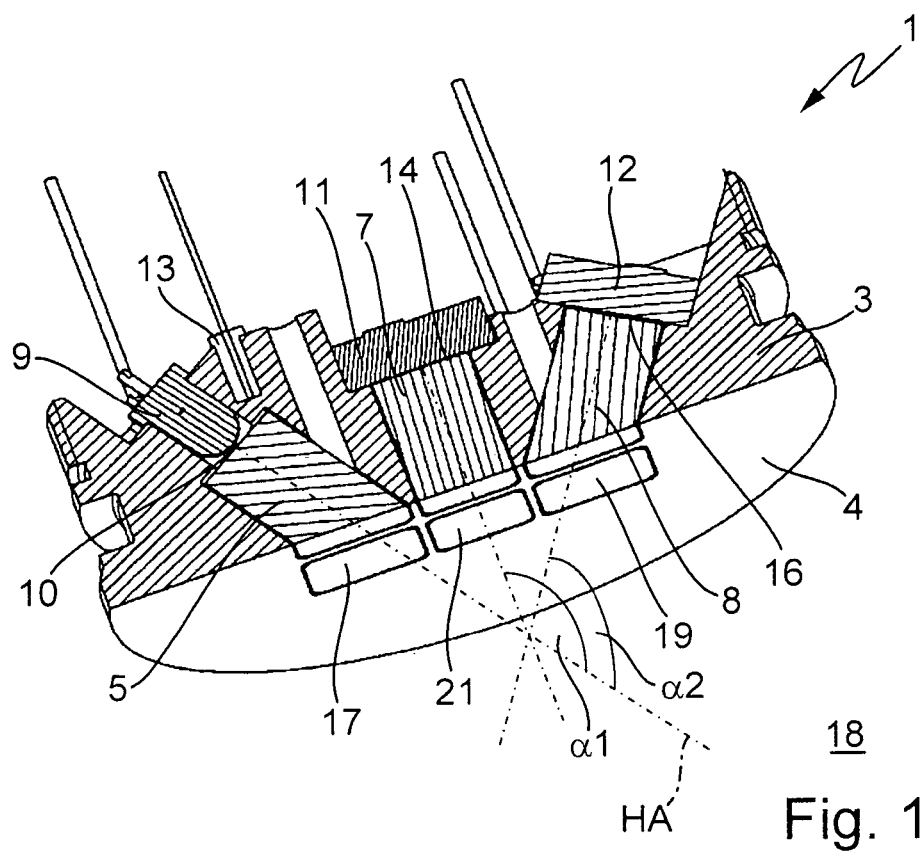
FIG. 1 is a section through an apparatus for measuring turbidity.
Figure 2:
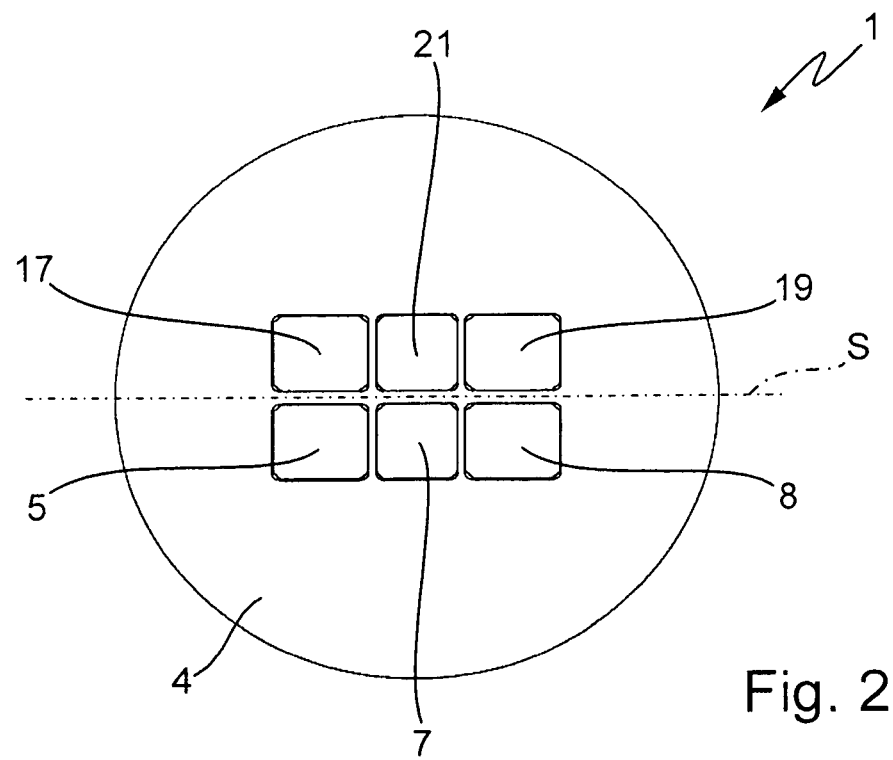
FIG. 2 is the apparatus of FIG. 1 in plan view.

FIGS. 1 and 2 show schematically in section (FIG. 1) and in plan view (FIG. 2) an apparatus 1 for turbidity measurement. The apparatus includes two emitters and four detectors. The cylindrical platform 3 includes a bore 5, which is oriented at an acute angle to a base 4 of the cylindrical platform 3. Within this bore 5 is arranged (serving as first emitter) a first light-emitting diode 9, whose end 10 is oriented in such a manner, that the central, main ray MR of a ray bundle emitted from the light-emitting diode 9 extends in the measured medium 18 at an angle of 45° to the base 4 of the cylindrical platform 3. In such case, the refraction of the light beam at the interface to the measured medium 18—and, in given cases, on a window (not shown) which is arranged between the measured medium 18 and light-emitting diode 9—is also taken into consideration. For the purpose of a simpler representation, the refraction of the main ray MR is not shown in FIG. 1.

Another bore 7, which is perpendicular to the base 4, serves to accommodate a first photodiode 11 as a first detector. The face 14 of the photodiode 11 is arranged in such a manner, that it can receive at an angle $\alpha 1$ of 135° to the main ray direction MR of the light-emitting diode 9 light scattered in the measured medium 18. The light refraction at an interface to the measured medium 18 (and, in given cases, at a window which is arranged between the measured medium 18 and light-emitting diode 9) is also taken into consideration here.

A third bore 8 forms a receptacle for a second photodiode 12, which serves as a further detector. The photodiode 12 is arranged in such a manner, that the normal of its face 16 is at an acute angle to the base 4. The second photodiode 12 is especially arranged in such a manner, that it can receive at an angle $\alpha 2$ of 90° to the main ray direction MR of the light-emitting diode 9 light scattered in the measured medium 18. The light refraction at the interface to the measured medium 18 (and, in given cases, at a window which is arranged between the measured medium 18 and the light-emitting diode 9) is also taken into consideration here.

Further accommodated in the platform 3 is a monitor diode 13, which, via another bore (not shown) in the cylindrical platform 3, can receive on direct paths light from the light-emitting diode 9. The propagation path of this light signal is selected in such a manner, that the light does not interact with a measured medium 18, in which the platform for turbidity measurement is immersed. The monitor diode 13 is a photodiode.

A second light-emitting diode and a third and fourth photodiode are arranged in an additional seat 17 (for the light-emitting diode) and in two additional seats 19, 21 (for the photodiodes) in the platform 3, as mirror images with respect to the mirror symmetry plane S (which is perpendicular to the base 4, and which extends along a diameter of the circularly shaped base 4), facing the first light-emitting diode 9 in the seat 5, as well as the photodiodes 11 and 12 in the seats 7 and 8. The mirror symmetry plane S especially runs parallel to the main ray direction MR of the first light-emitting diode 9 and to that of the light-emitting diode (not shown) arranged in the bore 17.

Associated with the second light-emitting diode (in the same manner as with the first light-emitting diode 9) can be another monitor diode, which is not shown here. Alternatively, one and the same monitor diode can also be associated with both light-emitting diodes. In the four beam, alternating light method, the two light-emitting diodes are alternately operated, so that a single monitor diode is sufficient for monitoring both light-emitting diodes.

Since the monitor diode, or the monitor diodes, receive(s) from the light-emitting diodes a direct light signal uninfluenced by the measured medium 18, such can especially be utilized for monitoring the photodiodes. A decrease in signal intensity due to aging is reflected in the detector signal of the monitor diode or diodes and can be detected by an electronic evaluating unit. The electronic evaluating unit can, in this case, cause the output of an alarm signal.

In the apparatus for turbidity measurement of FIGS. 1 and 2, two emitter/detector arrangements, so called "channels", are implemented for turbidity measurements according to the four beam, alternating light method.

The first channel forms the arrangement referred to in the following as the 135° channel, this channel comprising the two light-emitting diodes arranged in the seats 5 and 17, and the first and second photodiodes arranged in the seats 7 and 21. In such case, the light-emitting diodes correspond to the first and second emitters, and the photodiodes to the first and second detectors of the previously described arrangement for performing the four beam, alternating light method. The second channel is referred to in the following as the 90° channel, and, in a corresponding manner, includes the two light-emitting diodes, as well as the third and fourth photodiodes, which are arranged in the seats 8 and 19.

For ascertaining the turbidity value, the emitters are alternately excited to emit light. In such case, the detector signals of the detectors of both channels can be registered simultaneously. The light paths for the 135° channel and the 9° channel are presented schematically in FIG. 3, and, for better perspicuity, are shown separately. The two emitters, which correspond to the light-emitting diode 9 and to the light-emitting diode arranged in the bore 17 in the apparatus in FIGS. 1 and 2, are here referenced with E1 and E2. The detectors of the 135° channel, which correspond to the photodiode 11 and the photodiode accommodated in the bore 21 and arranged mirror-symmetrically to the photodiode 11, are referenced with D1 and D2. The detectors of the 90° channel, which correspond to the photodiode 12 and the photodiode accommodated in the bore 19 and arranged mirror-symmetrically to the photodiode 12, are referenced with D3 and D4.

If the first emitter E1 is excited to emit light, the first detector D1 of the 135° channel then receives a light signal along the propagation path 1_1, and the second detector D2 of the 135° channel along the propagation path 2_1. At the same time, the detectors of the 90° channel receive light signals, namely the third detector D3 along the propagation path 3_1, and the fourth detector D4 along the propagation path 4_1.

If the second emitter is excited to emit light, the first detector of the 135° channel receives a light signal along the propagation path 1_2, and the second detector of the 135° channel along the propagation path 2_2. At the same time, the third detector D3 receives a light signal from the emitter E2 along the propagation path 3_2, and the fourth detector D4 along the propagation path 4_2.

All propagation paths are, in this case, indirect propagation paths, in the case of which the detectors receive from the respective active emitter light signals scattered on dispersed particles of the measured medium.

Photodiodes which are applied as detectors produce from the received light signals a photovoltage or a photocurrent. The photovoltage or the photocurrent is further processed for ascertaining a turbidity value. As previously described, from the photovoltage or the photocurrent, values can be derived (for example, digitized values) which are then used for ascertaining a turbidity value. The photovoltage or the photocurrent as immediate detector signals, as well as values derived therefrom, are, as already previously defined, included under the terminology, "detector signal".

From the detector signals of the detectors D1 and D2, a first turbidity value for the 135° channel can be ascertained according to the formula $$W_1 = \frac{I_{1\_1} \cdot I_{2\_2}}{I_{1\_2} \cdot I_{2\_1}} \quad (1)$$

In such case, $I_{1\_1}$ is the detector signal of the first detector in the case of excitation of the first emitter, $I_{1\_2}$ is the detector signal of the first detector in the case of excitation of the second emitter, $I_{2\_1}$ is the detector signal of the second detector in the case of excitation the first emitter, and $I_{2\_2}$ is the detector signal of the second detector in the case of excitation of the second emitter.

In an analogous manner, from the detector signals of the detectors D3 and D4, a four beam-alternating light turbidity value can be ascertained for the 90° channel according to the formula $$W_1 = \frac{I_{3\_1} \cdot I_{4\_2}}{I_{3\_2} \cdot I_{4\_1}} \quad (2)$$

wherein $I_{3\_1}$ is the detector signal of the third detector in the case of excitation of the first emitter, $I_{4\_2}$ is the detector signal of the fourth detector in the case of excitation of the second emitter, $I_{3\_2}$ is the detector signal of the third detector in the case of excitation of the second emitter, and $I_{4\_1}$ is the detector signal of the fourth detector in the case of excitation of the first emitter.

In addition to the solids concentration in the measured medium, the turbidity value also depends on the size of the dispersed particles, and on the angle at which the scattered light is registered. Therefore, the described apparatus for turbidity measurement must not only be in each case individually calibrated for the 135° channel and the 90° channel, but also, in each case, with respect to the measured medium to be examined.

Figure 4A:
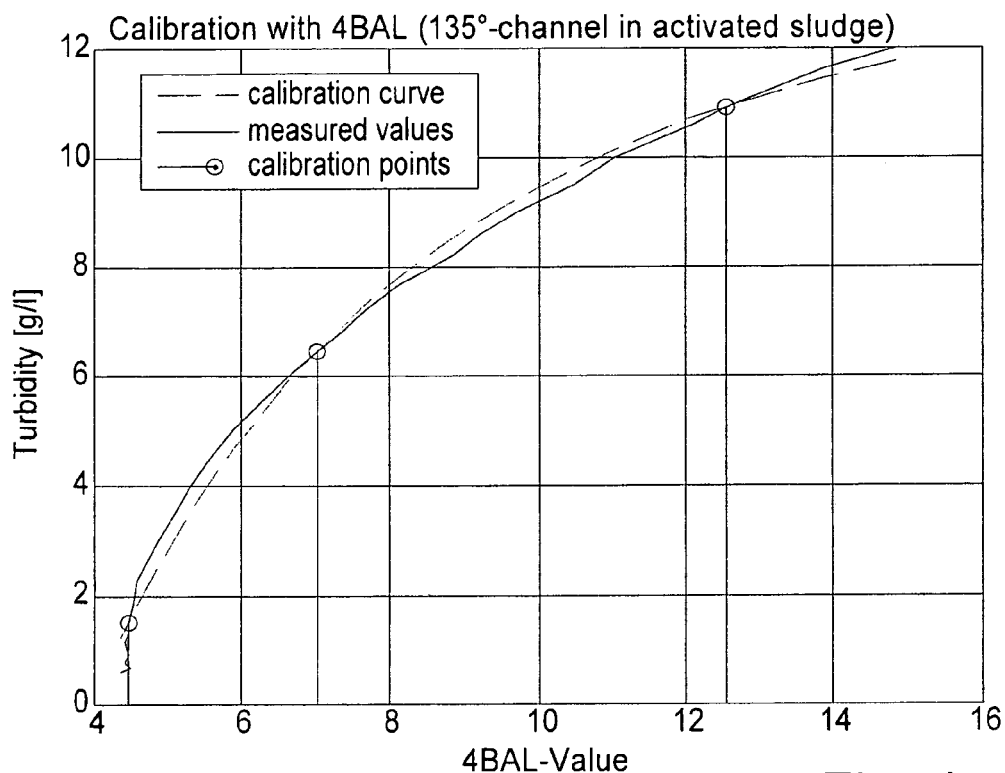
FIG. 4 shows three calibration curves for calibrating the apparatus of FIG. 1 in different measured media.
Figure 4B:
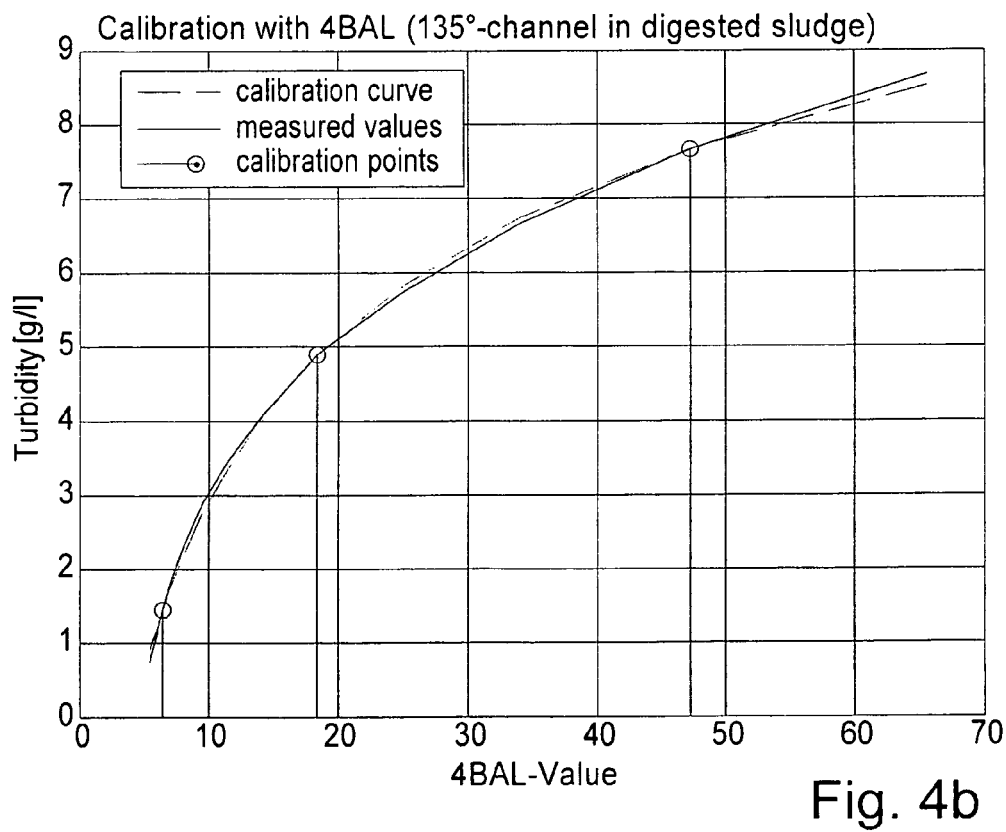
Figure 4C:
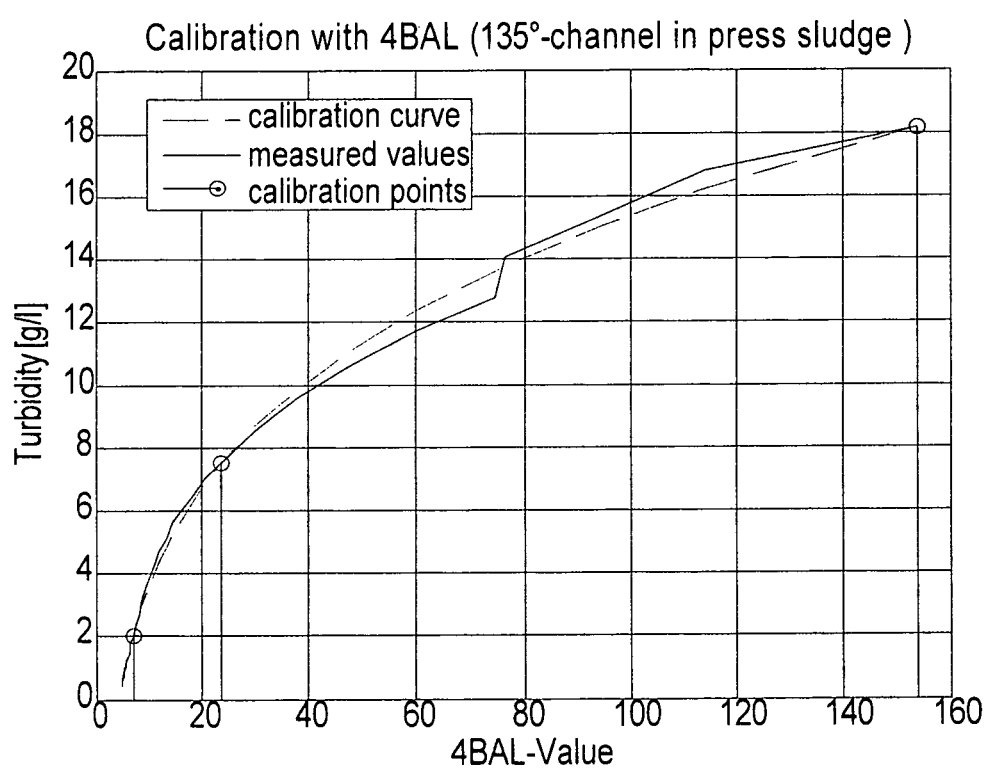

FIG. 4 shows example calibration curves for the 135° channel (by evaluating the detector signals of the first and second detectors) in three different measured media, namely in activated sludge (FIG. 4*a*), in digested sludge (FIG. 4*b*) and in press sludge (FIG. 4*c*). The calibration curves are presented in graphs, in the case of which the turbidity value (four beam, alternating light, or 4 BAL, value) calculated according to formula (1) is plotted on the abscissa, and the solids concentration in g/l is plotted on the ordinate.

In such case, in the present example, three points (which are marked by circles) are utilized for the calibrating. The solids curve shows the values measured in the calibration medium. The calibration curve ascertained from the three calibration points is shown with a dashed line. In the present case, the best approximation of the measurement curve results from taking the logarithm of the measured values and subsequent fitting of a polynomial of third degree.

The 90° channel is calibrated in analogous manner. In such case, due to the different scattering angle, different calibration curves will result than those for the 135° channel. This means that the calibration curves for the 90° channel are independent of the calibration parameters of the 135° channel.

For ascertaining the turbidity of a measured medium, two different turbidity values according to the four beam, alternating light method can thus be ascertained from the detector signals of the four detectors D1 through D4. The associated turbidity values or solids concentrations are ascertained according to the described calibration curves, which are independent of one another. This evaluation can occur by means of an electronic evaluating unit.

So long as essentially identical solids concentrations are ascertained by means of both channels, these values can be assumed to be plausible. The solids concentrations can then be averaged, or only one, or both, can be output as the measurement result.

If, however, a turbidity value or a solids concentration fluctuates, for example, strongly for a short period of time, measured value plausibility is no longer given. This can, for example, be the case when a large particle comes into a propagation path of the four beam, alternating light arrangement. In this case, there results a stronger deviation in the ascertained solids concentrations of both channels from one another. If such a deviation is recognized—for example, by taking the difference of the two solids concentrations and comparing it with a predetermined threshold value for this difference—an alarm signal of the evaluating unit can be output. The measuring is then repeated after a short time, and the difference of the newly ascertained turbidity values is again compared with the threshold value. If the difference falls beneath the threshold value, a measurement result, for example, an average value of the ascertained solids concentrations of both channels is output.

A further possible scenario is that the two solids concentrations ascertained from the different channels deviate from one another at an essentially constant, non-negligible magnitude over a longer period of time. If such a behavior is detected, the probability is very large that the channels are non-uniformly fouled. In this case, an alarm which displays that a cleaning of the sensor is required can be output by the evaluating unit. Alternatively or additionally, a cleaning can automatically be set in motion by the evaluating unit. Means for automatic cleaning of a turbidity sensor (for example, as described in DE 41 42 938 C2) are known to those skilled in the art.

Other effects, such as component aging or an essentially uniform fouling of the total arrangement can be registered by additional monitoring of the individual detector signals.

Figure 3A:
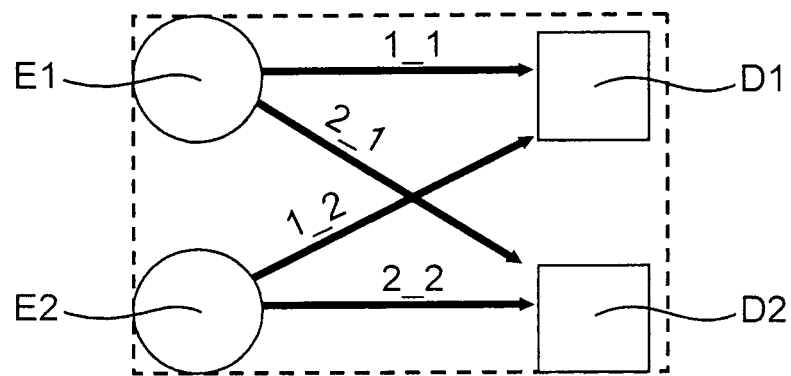
FIG. 3 is the propagation paths of the light signals transmitted from the emitters in the four beam, alternating light method.
Figure 3B:
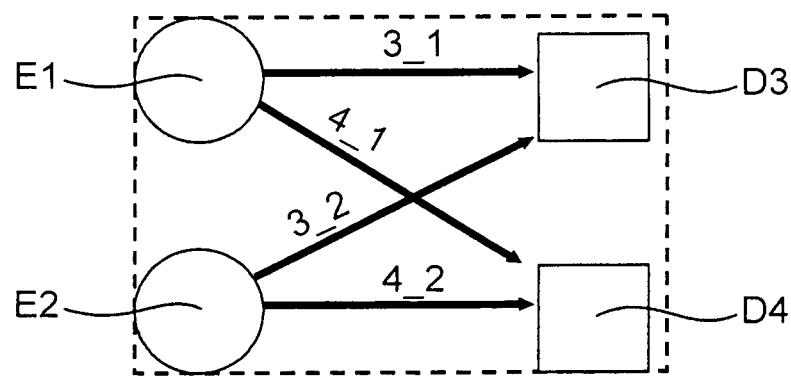
Figure 5:
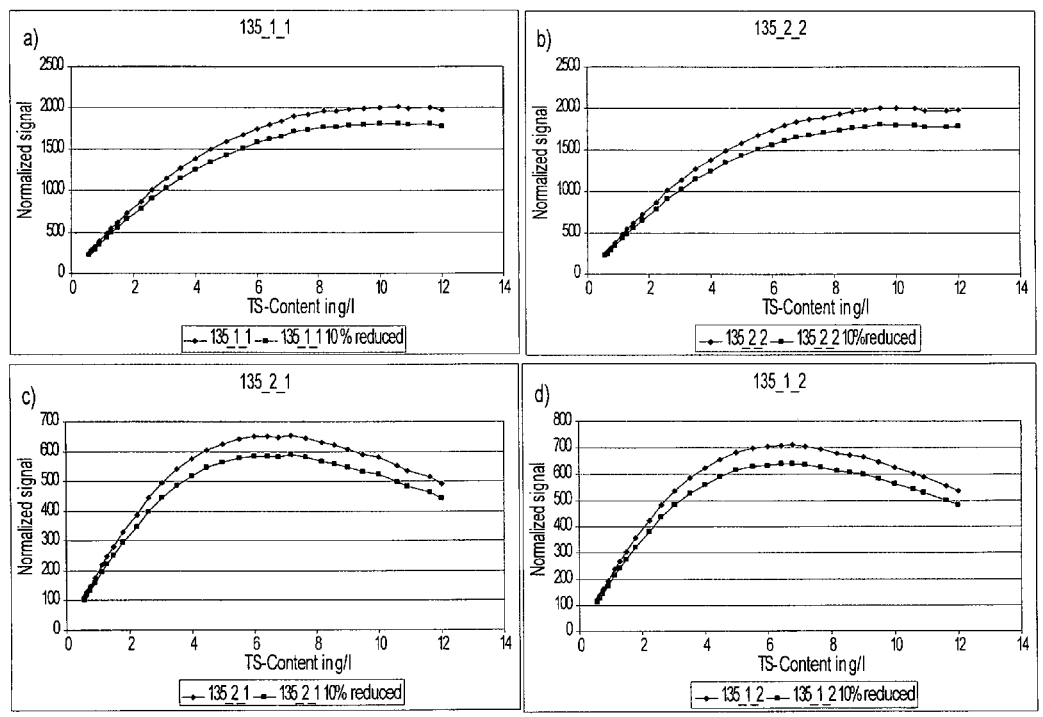
FIG. 5 shows detector signals of a turbidity measurement according to the four beam, alternating light method as a function of solids content.

In FIG. 5, by way of example, the four detector signals of the 135° channel are shown, which correspond to the four propagation paths illustrated in FIG. 3*a*), in the case of a solids content of up to 12 g/l activated sludge. On the abscissa, the solids content (TS content) is given in g/l, and on the ordinate is given a normalized signal intensity of the detector signal. FIG. 5*a*) shows the D1 detector signal corresponding to the propagation path 1_1, FIG. 5*b*) the D2 detector signal corresponding to the propagation path 2_2), FIG. 5*c* the D2 detector signal corresponding to the propagation path 2_1, and FIG. 5*d*) the D1 detector signal corresponding to the propagation path 1_2. In such case, the diamond-shaped points in each case show the curve of the detector signal in the case of an emitter power of 100% and an optimal signal yield for the detectors. The square points show the four detector signals in the same measured medium in the case of equal solids content, and in the case of a uniform lessening in the signal strength, here of 10%. Such a uniform lessening of the incoming signal for the detector can occur, for example, through uniform fouling of the sensor.

Figure 6:
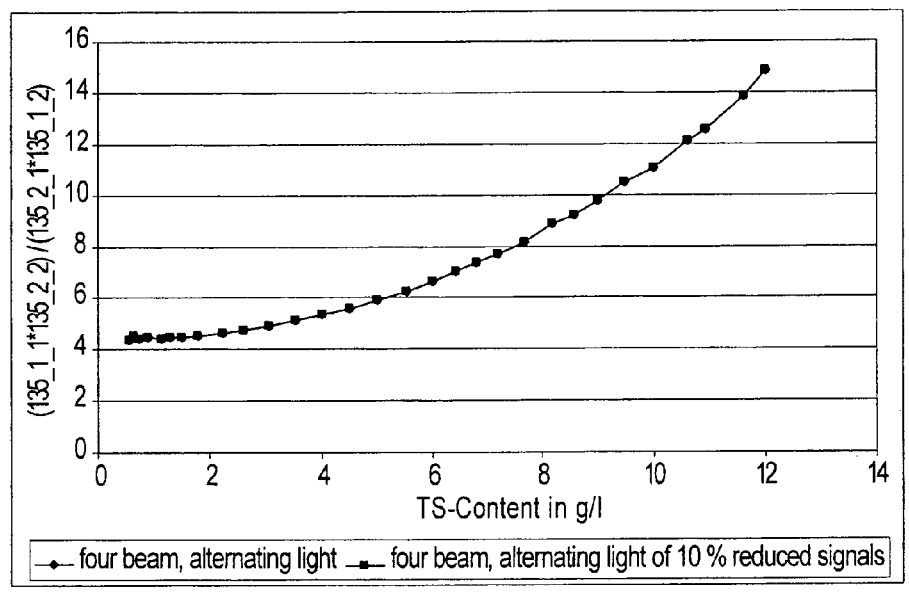
FIG. 6 shows turbidity value as ascertained from the detector signals of FIG. 4.

In FIG. 6, the turbidity value ascertained from the individual detector signals illustrated in FIG. 5 according to the formula (1) is plotted as a function of the associated solids concentration (TS content) in g/l. The diamond-shaped points again represent the turbidity values obtained in the case of 100% signal yield, while the square points represent turbidity values which were ascertained from the individual detector signals weakened by 10%. Although the individual signals show clearly different curves in the case of an emitter power of 100% compared to the case of a signal strength lessened by 10%, this difference is not evident in the turbidity value ascertained according to the four beam, alternating light method under application of the formula (1). This is due to the already previously described relative robustness of the four beam, alternating light method with regard to slight disturbances.

For monitoring a uniform disturbance of the sensor (for example, through component aging or due to a uniform fouling), the monitoring of individual detector signals, thus, can provide valuable supplemental information, and a disturbance can then be recognized early and eliminated, or an estimation of the further lifespan of a component can be performed.

For this, a number n of the ascertained individual detector signals is selected (in the example of the apparatus according to FIGS. 1 and 2, these are a maximum of 8 signals). The number n is, in such case, smaller or equal to the number of all registered detector signals. From these detector signals, a measured value vector or a measured value point is formed, whose components form the n individual detector signals. The measured value vector is represented in an n-dimensional vector space, and the measured value point is correspondingly formed in an n-dimensional coordinate system. Both representations are equivalent.

Figure 7:
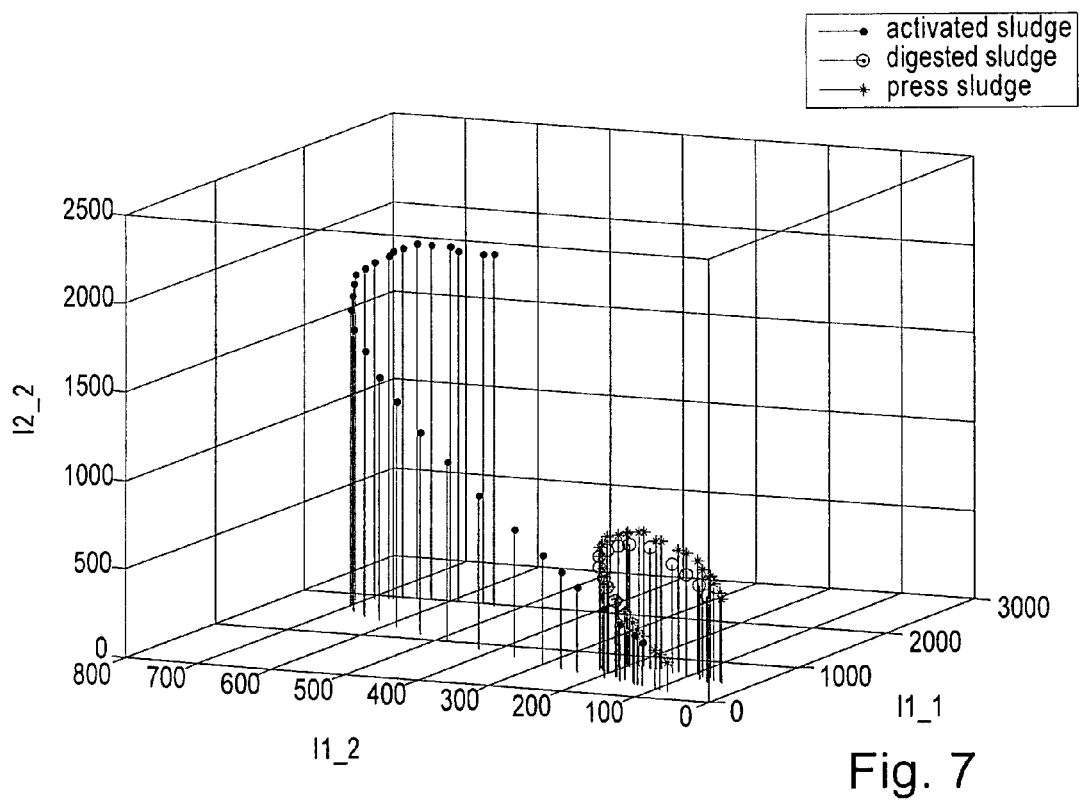
FIG. 7 is a graph of measurement points formed from three detector signals as coordinates in a three dimensional coordinate system.

An example is shown in FIG. 7. Here, in a three dimensional coordinate system, three of a total of four individual detector signals of the 135° channel in the case of measurements in different measured media are shown. The three illustrated detector signals correspond to the propagation paths 1_1, 1_2 and 2_2 in the schema illustrated in FIG. 3*a*). The measured media are activated sludge (points), digested sludge (circles) and press sludge (stars). The individual measured value points correspond to different solids concentrations.

It may be recognized that all so-obtained measured value points lie on one plane, although measurement occurred in very different media.

In the general case, when using the detector signals of all detectors, the monitor diode and the turbidity value ascertained from the single channels according to the four beam, alternating light method, a surface or an n-dimensional region within the n-dimensional vector space is modeled or learned with machine learning methods. In the example in FIG. 7, this n-dimensional region is thus a plane on which all measured value points lie.

A new measured value vector or point can then be diagnostically evaluated, in that a distance of the vector or point from the estimated or learned region (in the example in FIG. 7, to the ascertained plane) is evaluated. Through such a method, measured value outliers can be detected, and, for example, the degree of fouling of individual channels also ascertained. From ascertaining the distance on the basis of the learned data, a probability can especially be ascertained with which the new measured value vector—and thus the last ascertained turbidity value—reflects the actual turbidity of the measured medium. This can be taken into consideration for plausibility checking the measured value.

By a continuous storing of the newly ascertained measured value vectors in a learning memory (especially in a neural network), the n-dimensional volume can always be modified further. In the case of a continuous disturbance of the system (e.g. through a uniform fouling of all individual propagation paths), the shape of the n-dimensional volume remains essentially preserved, but is, however, shifted within the n-dimensional space.

In the case of aging of a component, e.g. a light-emitting diode, both a shifting as well as a compression or stretching of the n-dimensional volume takes place. The type of distortion of the n-dimensional volume can be evaluated by a learning method or by a model, and in such a manner, that, from the distortion, the type of disturbance can directly be inferred, and, in given cases, suitable countermeasures such as cleaning or component replacement can automatically be undertaken.

In an alternative or additional method, an option is to allow the learning memory (especially the neural network) to learn different n-dimensional regions which correspond to different possible disturbances. A newly ascertained n-dimensional measured value point can then be compared with the different n-dimensional regions that are associated with various disturbances, and a probability can be ascertained, with which one of the various disturbances is present.

The invention claimed is:

1. A method for turbidity measurement in a measured medium by means of an apparatus comprising: at least a first and a second emitter, and at least a first detector and a second detector, comprising the steps of:
   exciting the first and the second emitter one after the other, in order to produce light signals directed into the measured medium, wherein each light signal travels along a first propagation path through the measured medium to the first detector, and is converted by such into a first detector signal; and travels along a second propagation path through the measured medium to the second detector, and is converted by such into a second detector signal; and
   ascertaining a turbidity value based on the first and the second detector signals by means of at least one additional detector, to which at least one of the light signals travels along an additional propagation path, a supplemental detector signal is ascertained, and on the basis of the additional detector signal, the turbidity value is checked as regards its plausibility, wherein:
   the plausibility is a probability with which the turbidity value reflects the actual turbidity of the measured medium; and
   the at least one additional detector receives light signal of at least one emitter along a propagation path outside of the measured medium.

2. The method as claimed in claim 1, wherein:
   the turbidity value is ascertained according to formula $$W_1 = \frac{I_{1\_1} \cdot I_{2\_2}}{I_{1\_2} \cdot I_{2\_1}}$$

wherein $I_{1\_1}$ is detector signal of the first detector (D1) in case of excitation of the first emitter (E1),
   wherein $I_{1\_2}$ is detector signal of the first detector (D1) in case of excitation of the second emitter (E2),
   wherein $I_{2\_1}$ is detector signal of the second detector (D2) in case of excitation of the first emitter (E1), and
   wherein $I_{2\_3}$ is detector signal of the second detector (D2) in case of excitation of the second emitter (E2).

3. The method as claimed in claim 1, further comprising the steps of:
   using a third and a fourth detector, to which light signal of the first emitter and of the second emitter respectively travel along a third propagation path through the measured medium and along a fourth propagation path through the measured medium;
   the third detector converts the light signal into a third detector signal, and the fourth detector converts the light signal into a fourth detector signal; and
   from the third and the fourth detector signal, an additional turbidity value is ascertained.

4. The method as claimed in claim 3, wherein:
   the additional turbidity value is ascertained according to formula $$W_1 = \frac{I_{3\_1} \cdot I_{4\_2}}{I_{3\_2} \cdot I_{4\_1}}$$

wherein $I_{3\_1}$ is detector signal of the third detector (D3) in case of excitation of the first emitter (E1),
   wherein $I_{4\_2}$ is detector signal of the fourth detector (D4) in case of excitation of the second emitter (E2),
   wherein $I_{3\_2}$ is detector signal of the third detector (D3) in case of excitation of the second emitter (E2), and
   wherein $I_{4\_1}$ is detector signal of the fourth detector (D4) in case of excitation of the first emitter (E1).

5. The method as claimed in claim 3, further comprising the step of:
   comprising the additional turbidity value with the turbidity value which is ascertained from the detector signals of the first and second detectors.

6. The method as claimed in claim 5, further comprising the step of:
   comparing the turbidity values with one another by ascertaining solids concentrations from the turbidity values and taking a difference between first and second solids concentrations; and
   for testing plausibility of the turbidity values, the difference between the solids concentrations is compared with a predetermined threshold value.

7. The method as claimed in claim 6, wherein:
   an error report is output when the difference exceeds the predetermined threshold value.

8. The method as claimed in claim 6, wherein:
   turbidity measurement is repeated when the difference exceeds the predetermined threshold value.

9. The method as claimed in claim 1, wherein:
   at least one of the detector signals is compared with a desired value.

10. The method as claimed in claim 1, wherein:
    from all detector signals which are used for ascertaining a turbidity value and/or from the at least one additional detector signal, a number of n detector signals is selected; and
    the selected detector signals are represented as coordinates of a measured value point in an n-dimensional coordinate system, or as components of a measured value vector in an n-dimensional vector space.

11. The method as claimed in claim 10, wherein:
    a distance of a measured value point or a measured value vector to a predetermined n-dimensional region of the point space or vector space is ascertained.

12. The method as claimed in claim 11, wherein:
    the predetermined n-dimensional region is ascertained from a model or is learned on basis of a machine learning method.

13. The method as claimed in claim 11, wherein:
    a newly ascertained measured value point or measured value vector is used for fitting the predetermined n-dimensional region.

14. The method as claimed in claim 11, wherein:
    on the basis of distance of the measured value point or the measured value vector from the predetermined n-dimensional region, a plausibility checking, especially a machine plausibility checking, of the turbidity value ascertained from the detector signals is performed.

15. An apparatus for measuring turbidity of a measured medium, comprising:
    at least a first and a second emitter wherein the first and second emitter are excited one after the other:
    at least a first and a second detector, said at least a first and at least a second emitter and said at least a first and at least a second detector are arranged with respect to one another in such a manner, that light signals produced by said at least a first and at least a second emitter and directed into the measured medium travel along a first propagation path through the measured medium to said at least the first detector, and along a second propagation path through the measured medium to said at least said second detector; and at least one additional detector, which is arranged in such a manner, that a light signal produced by said at least one first and at least one second emitter travels along an additional propagation path to said at least one additional detector, wherein:

said at least one additional detector is arranged with respect to said at least a first and said at least a second emitter in such a way, that it receives a light signal of at least one of said at least a first and said at least a second emitter along a propagation path outside of the measured medium; and an evaluating unit, which is designed to determine a turbidity value of the measured medium from detector signals of said at least one first and at least one second detector;

said evaluating unit is furthermore designed to check, on basis of a detector signal produced by said at least one additional detector, the turbidity value as regards its plausibility; and the plausibility is a probability with which the turbidity value reflects the actual turbidity of the measured medium.

16. The apparatus as claimed in claim 15, wherein:
said at least a first emitter and said at least a first detector are arranged next to one another; and said at least a second emitter and said at least a second detector are arranged as mirror images of said at least a first emitter and said at least a first detector.

17. The apparatus as claimed in claim 16, wherein:
a third and a fourth detector of said at least one additional are arranged in such a manner, that said at least a second emitter, said at least a second detector and said fourth detector are arranged as mirror images to said at least a first emitter, said at least a first detector and said third detector.

18. The apparatus as claimed in claim 17, wherein:
said at least a first emitter is designed in its excited state to direct a light beam, especially a light ray bundle with a main ray direction (MR), into the measured medium;

the normal of a face of said at least a first detector is arranged at a first angle to the main ray direction;

the normal of a face of said third detector is arranged at a second angle to the main ray direction; and said first angle differs from said second angle.

19. The apparatus as claimed in claim 15, wherein:
said at least a first and at least a second emitter are light-emitting diodes, and said at least a first, said at least a second and said at least one additional detector are photodiodes.

20. The apparatus as claimed in claim 15, wherein:
said evaluating unit has a learning memory, especially a neural network.

* * * * *